(12) United States Patent
Maeda et al.

(10) Patent No.: US 8,574,891 B2
(45) Date of Patent: Nov. 5, 2013

(54) NUCLEIC ACID ANALYZER, AUTOMATIC ANALYZER, AND ANALYSIS METHOD

(75) Inventors: Kohshi Maeda, Tokai (JP); Masato Ishizawa, Hitachinaka (JP); Minoru Sano, Hitachinaka (JP); Hironori Kaji, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 57 days.

(21) Appl. No.: 13/000,579

(22) PCT Filed: Jun. 17, 2009

(86) PCT No.: PCT/JP2009/061004
§ 371 (c)(1),
(2), (4) Date: Dec. 21, 2010

(87) PCT Pub. No.: WO2009/157353
PCT Pub. Date: Dec. 30, 2009

(65) Prior Publication Data
US 2011/0104703 A1    May 5, 2011

(30) Foreign Application Priority Data
Jun. 23, 2008  (JP) .................................. 2008-162669

(51) Int. Cl.
| | | |
|---|---|---|
| C12M 1/34 | (2006.01) | |
| C12M 3/00 | (2006.01) | |
| C12M 1/00 | (2006.01) | |
| C12Q 1/68 | (2006.01) | |
| G01N 15/06 | (2006.01) | |
| G01N 33/00 | (2006.01) | |
| G01N 33/48 | (2006.01) | |

(52) U.S. Cl.
USPC ............... 435/287.1; 435/283.1; 435/287.2; 422/50; 422/68.1

(58) Field of Classification Search
USPC .............. 435/6.1, 6.11, 6.12, 7.1, 91.1, 91.2, 435/91.51, 283.1, 287.1, 287.2; 436/94, 436/501; 536/23.1, 24.3, 24.33, 25.3; 422/50, 68.1
See application file for complete search history.

(56) References Cited

U.S. PATENT DOCUMENTS

| | | |
|---|---|---|
| 5,038,852 A | 8/1991 | Johnson et al. |
| 5,736,106 A | 4/1998 | Ishiguro et al. |
| 5,795,748 A | 8/1998 | Cottingham |
| 6,413,780 B1 | 7/2002 | Bach et al. |
| 2002/0081669 A1 | 6/2002 | Festoc |

FOREIGN PATENT DOCUMENTS

| | | |
|---|---|---|
| EP | 0 236 069 | 9/1987 |
| JP | 62-240862 | 10/1987 |
| JP | 03-262499 | 11/1991 |
| JP | 06-277036 | 10/1994 |
| JP | 06-281655 | 10/1994 |
| JP | 8-196299 | 8/1996 |
| JP | 08-271524 | 10/1996 |
| JP | 10-127268 | 5/1998 |
| JP | 2003-050242 | 2/2003 |
| JP | 2003-522322 | 7/2003 |
| JP | 2004-504828 | 2/2004 |
| JP | 2005-125311 | 5/2005 |
| WO | WO 00/21668 | 4/2000 |
| WO | WO 02/09877 A1 | 2/2002 |

*Primary Examiner* — Frank Lu
(74) *Attorney, Agent, or Firm* — McDermott Will & Emery LLP

(57) ABSTRACT

This invention relates to a nucleic acid analyzer comprising: reaction containers capable of containing nucleic-acid-containing samples and reagents; an incubation mechanism capable of controlling temperatures of reaction containers set at different levels; an analysis mechanism for analyzing the samples contained in the reaction containers; and a transport mechanism for transporting a reaction container. In accordance with the assay technique to be performed on a nucleic-acid-containing sample, the transport mechanism transports a reaction container to a given incubation mechanism in a given order. The reaction container subjected to the process of sample preparation is transported to the analysis mechanism at a given time and the sample is analyzed.

7 Claims, 5 Drawing Sheets

(a)

(b)

NUCLEIC ACID ANALYZER, AUTOMATIC ANALYZER, AND ANALYSIS METHOD

RELATED APPLICATIONS

This application is the U.S. National Phase under 35 U.S.C. §371 of International Application No. PCT/JP2009/061004, filed on Jun. 17, 2009, which in turn claims the benefit of Japanese Application No. 2008-162669, filed on Jun. 23, 2008, the disclosures of which Applications are incorporated by reference herein.

TECHNICAL FIELD

The present invention relates to an analysis method comprising qualitative or quantitative analysis of a target nucleic acid contained in a biological sample, such as blood or urine, which requires temperature changes during the process of sample preparation.

BACKGROUND ART

Examples of analysis methods that require temperature changes during the process of sample preparation include isothermal gene amplification techniques such as NASBA, LAMP, and TMA. Such gene amplification techniques necessitate a process of changing nucleic acid conformation via heating prior to the amplification reaction, in order to attain stable analysis results. Since a nucleic acid amplifying enzyme is likely to lose activity at high temperatures, a process of cooling the heated reaction solution to at least the reaction temperature for enzyme amplification is further required. Also, the speed of such temperature changes is associated with analysis duration or efficiency of a nucleic acid conformational change. Accordingly, it is preferable that such temperature changes be completed rapidly.

The aforementioned analysis methods generally involve the use of the Peltier device in order to realize rapid temperature changes, and these methods realize rapid temperature changes using voltage shifts. In order to efficiently realize such temperature changes for a plurality of samples, further, it was general practice to prepare samples by a batch process that collectively treats a plurality of samples.

JP Patent Publication (kokai) No. 06-281655 A (1994) or 08-271524 A (1996) discloses an automatic analyzer that analyzes blood or the like with the use of an antigen-antibody reaction and comprises a plurality of incubators.

JP Patent Publication (kokai) No. 06-277036 A (1994) discloses an incubator that controls the temperature of a nucleic acid sample by transporting a reaction block carrying a plurality of tubes between a heating block and a cooling block and bringing the lower surface of the reaction block into contact with the heating or cooling block.

PRIOR ART DOCUMENTS

Patent Documents

Patent document 1: JP Patent Publication (kokai) No. 06-281655 A (1994)

Patent document 2: JP Patent Publication (kokai) No. 08-271524 A (1996)

Patent document 3: JP Patent Publication (kokai) No. 06-277036 A (1994)

SUMMARY OF THE INVENTION

Problem to be Solved by the Invention

Conventional analysis methods requiring two or more temperature changes in the process of sample preparation involve the use of the Peltier device to realize rapid heating or cooling, and rapid temperature changes are realized using voltage shifts. In order to realize such temperature changes efficiently, however, a plurality of samples were collectively treated according to conventional analysis methods, and a plurality of samples had to be processed collectively in all analysis steps. When temperature changes during the process of sample preparation differ depending on assay, or when the reaction time or detection time varies depending on assay, accordingly, different assays could not be simultaneously performed.

Since a plurality of samples were collectively treated, it was difficult to completely synchronize the duration from reagent addition to temperature changes or the duration from temperature changes to enzyme addition among a plurality of samples. This was a factor that would increase variations in detection results.

It is an object of the present invention to provide a nucleic acid analyzer that allows performance of different assays on a plurality of samples.

Means for Attaining the Object

The present invention relates to a nucleic acid analyzer comprising: reaction containers that can contain nucleic-acid-containing samples and reagents; an incubation mechanism that can control the temperatures of reaction containers maintained at different levels, an analysis mechanism that analyzes the sample contained in a reaction container; and a transport mechanism that transports a reaction container. In accordance with the assay technique to be performed on a nucleic-acid-containing sample, the transport mechanism transports a reaction container to a given incubation mechanism in a given order. Thus, temperature changes can be made to samples in accordance with relevant assay techniques. The reaction container subjected to the process of sample preparation is transported to the analysis mechanism at a given time, and the sample is then analyzed.

Effects of the Invention

According to the present invention, reaction containers can be subjected to continuous analysis even when assays involving different temperature changes during the process of preparation of sample solutions or assays involving different reaction or detection times or detection intervals are performed.

EMBODIMENTS FOR CARRYING OUT THE INVENTION

Figure 1:
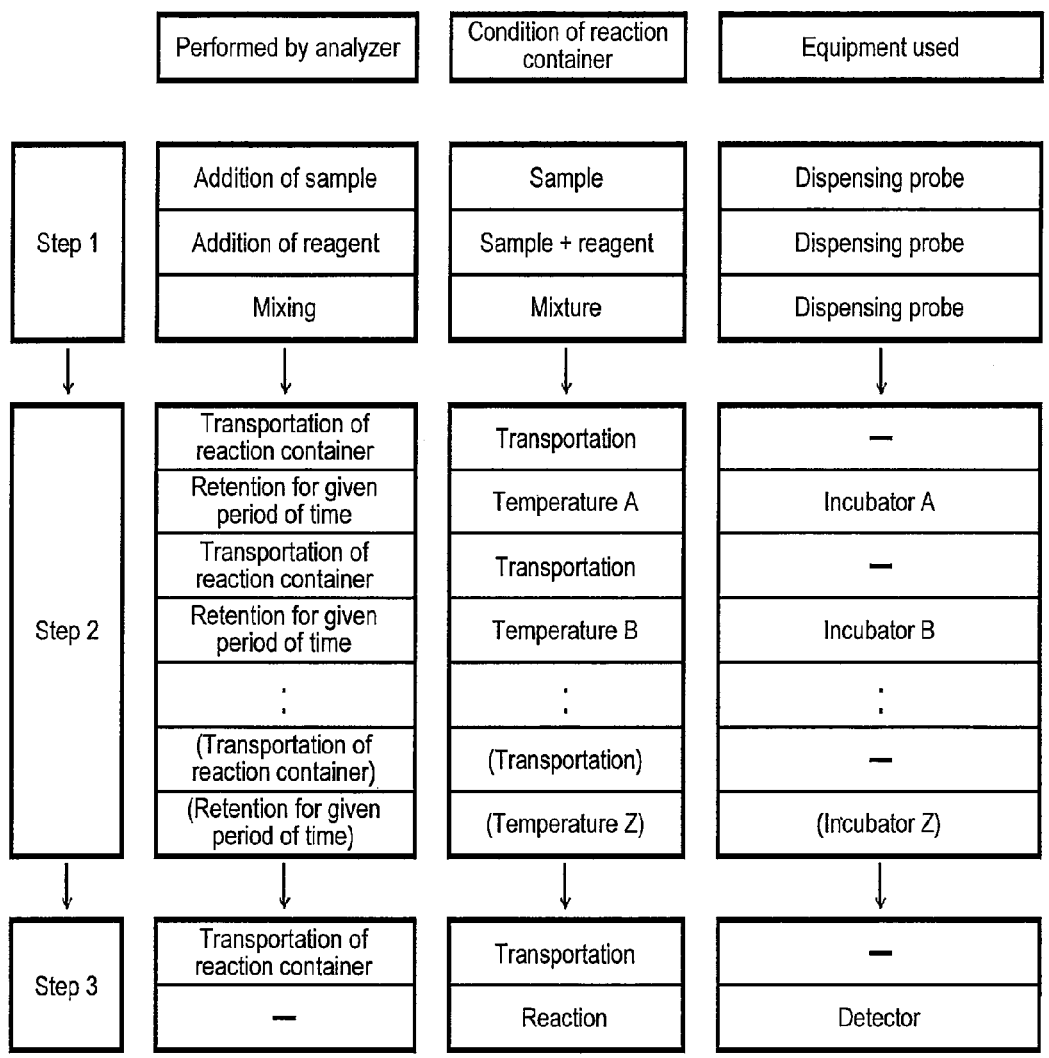
FIG. 1 is a schematic flow diagram illustrating analysis operations in the examples.

The examples disclose an analysis method requiring two or more temperature changes in the process of sample preparation (i.e., the process of reaction solution preparation) with the use of two or more different incubators set at temperatures required for assays, a dispensing probe for preparing a sample, and a detector for detecting a target substance, wherein the method performs analysis by at least the following 3 steps.

1) A step of preparing a reaction solution by mixing a sample and a reagent with the use of a dispensing probe;
2) a step of transporting a reaction container between two or more incubators set at temperatures required for assays to perform temperature changes in the process of reaction solution preparation; and
3) a step of detecting a target substance (a target nucleic acid).

It is not necessary to carry out Step 1 of reaction solution preparation prior to Step 2. Step 1 may be carried out at any time, provided that it is carried out prior to Step 3 of target nucleic acid detection. Step 1 may be carried out before or after Step 2, both before and after Step 2, or during Step 2.

The examples disclose an automatic analyzer used for an analysis method requiring two or more temperature changes in the process of reaction solution preparation, which comprises two or more different incubators set at temperatures required for assays, a dispensing probe for preparing a sample, a mechanism for transporting a reaction container, and a detector for detecting a target nucleic acid, and it analyzes a sample by making use of at least the following 3 functions.

1) A function of preparing a reaction solution by mixing a sample and a reagent with the use of a dispensing probe;
2) a function of transporting a reaction container between incubators set at temperatures required for assays by means of a mechanism for transporting a reaction container; and
3) a function of detecting a target nucleic acid with a detector.

It is not necessary to exert function 1 of reaction solution preparation before the temperature is changed, and it may be exerted at any time, provided that it is exerted before function 3 of target substance detection is exerted. Function 1 can be exerted before or after exertion of function 2, both before and after exertion of function 2, or during exertion of function 2.

Any detector may be used to detect a target nucleic acid, provided that reaction containers can be continuously introduced and analytical reactions in the reaction containers can be detected. A preferable detector is that of a rotary-disc system, and it allows reaction containers to be continuously introduced thereinto from a given position. A more preferable detector is capable of detecting the reaction process with the elapse of time and automatically discarding reaction containers after the completion of detection. The detection method and the detection mechanism of the detector vary depending on analysis method, and any method and mechanism may be employed, provided that they allow a target nucleic acid to be qualitatively or quantitatively detected.

The examples disclose a nucleic acid analyzer comprising: a plurality of reaction containers that can contain nucleic-acid-containing samples and reagents; a plurality of incubation mechanisms that can control the temperatures of reaction containers set at different levels; an analysis mechanism that analyzes the samples contained in reaction containers; a transport mechanism that transports reaction containers to a given incubation mechanism; and a control mechanism that controls the transport mechanism. The transport mechanism transports reaction containers to a given incubation mechanism in a given order in accordance with the assay to be performed on a nucleic-acid-containing sample of interest.

The examples also disclose an analysis method using a nucleic acid analyzer, wherein a plurality of incubation mechanisms that can control the temperatures of reaction containers set at different levels and reaction containers that contain nucleic-acid-containing samples and reagents are prepared;

the reaction container is transported to an incubation mechanism of interest in accordance with the assay technique to be performed on the nucleic-acid-containing sample, the incubation mechanism controls the temperature of the reaction container, the reaction container is transported to another incubation mechanism of interest, the incubation mechanism controls the temperature of the reaction container so as to maintain it at a different level, and the reaction container is transported to the incubation mechanism in the order as desired to change the temperature of the sample as desired; and the reaction container is transported to the analysis mechanism to analyze the sample.

The examples disclose that the analysis mechanism is capable of detecting the analytical reaction of a sample with the elapse of time.

The examples disclose that the analysis mechanism comprises a rotary disc capable of containing a plurality of reaction containers.

The examples also disclose that the transport mechanism transports a reaction container to an incubation mechanism and an analysis mechanism of interest.

In addition, the examples disclose that the sample and the reagent contained in the reaction container are agitated.

The examples disclose that the temperature of the reaction container is controlled by the incubation mechanism, and the sample and the reagent are then agitated.

Also, the examples disclose that, depending on the temperature of the sample before it has been transported to the incubation mechanism, the duration during which the reaction container containing such sample is controlled by the incubation mechanism is altered.

Further, the examples disclose that, depending on the incubation mechanism to which the reaction container was transported before it has been transported to the analysis mechanism, the duration of transportation from the incubation mechanism to the analytical mechanism is altered.

Hereafter, the novel characteristics and effects of the present invention are described in detail with reference to the drawings, although the technical scope of the present invention is not limited to concrete examples provided below.

Example 1

This example involves the use of a dispensing probe for preparing a sample, two or more different incubators set at temperatures required for assays, and a detector for detecting a target substance.

Any dispensing probe may be used for sample preparation, provided that it can accurately dispense the sample and the reagent. Use of an exchangeable and removable dispensing chip is preferable for the purpose of prevention of sample contamination. Specific examples include Pipetman pipettes (Gilson) and electronic pipettes (Biohit).

Any incubators may be used as the two or more different incubators set at temperatures required for assays, provided that the reaction containers are capable of adhering to the incubator within the range of the reaction solutions, and the temperature can be set at a level required for assays. When the target temperature is higher than room temperature, a heating incubator is used. When the target temperature is lower than room temperature, a cooling incubator is used.

Any detector may be used for detecting a target substance, provided that such detector is capable of detecting a target substance. The detection method and the detection mechanism of the detector vary depending on analysis method. More preferably, a detector is capable of detecting the analytical reaction in the reaction container with the elapse of time. When fluorescence emission is to be analyzed, specifically, the detector is composed of an excitation light applicator for exciting fluorescence emission and a sensor for detecting excited light, so as to detect fluorescence emission.

This example involves the use of above 3 forms of equipment and implementation of the following 3 processes to analyze the target substance.

1) A step of preparing a reaction solution by mixing a sample and a reagent with the use of a dispensing probe;

2) a step of transporting a reaction container between two or more incubators set at temperatures required for assays to perform temperature changes in the process of reaction solution preparation; and 3) a step of detecting a target substance.

Hereafter, the above steps are described in detail with the use of concrete examples with reference to FIG. 1.

In Step 1, a sample container containing a test sample derived from a biological sample is used. The sample is removed from the sample container with the use of a dispensing probe and dispensed into a reaction container. Subsequently, a reagent is removed from a reagent container and dispensed into a reaction container. The sample and the reagent are then mixed by repeating suction and ejection with a dispensing probe in the reaction container. More preferably, a dispensing chip is exchanged with another chip for each sample or reagent dispensing operation in order to prevent the sample or reagent from contamination. In this process, the sample container can be used as a reaction container, as long as the amount of the sample in the sample container is large enough for detection. In such a case, the process of removing the sample from the sample container and dispensing the same into reaction container can be omitted. Also, mixing may be carried out in the reaction container with the use of a mixing agitator.

The term "biological sample" used herein refers to a sample obtained by physical examination, such as health screening, medical check-up, multiphasic health screening, or health screening by mail; a biological sample containing the target substance in the blood, tissue, or urine of an outpatient or inpatient obtained at a hospital; and a sample to which such biological sample is adhered.

The term "target substance" used herein refers to a component derived from any organism (including a virus or a microorganism), and the term preferably refers to a protein, a peptide, an amino acid, or a nucleic acid. A test sample may be obtained by subjecting a biological sample to a pretreatment such as purification. A specific example of the pretreatment is, when the target substance is a viral nucleic acid, purification of such nucleic acid from a biological sample. For example, a nucleic acid component is separated from a protein component with the use of phenol and chloroform to purify a nucleic acid. Alternatively, a nucleic acid is allowed to adsorb to a silica column, washed, and then eluted from the silica column with the use of a nucleic-acid-dissolving solution. Thus, a nucleic acid is purified.

As the sample container, the reaction container, and the reagent container used herein, any container may be used, provided that components of the container are not transferred to the sample, the reagent, or the reaction solution. Preferably, a transparent polypropylene container is used. Specific examples include a 1.5-ml Eppendorf tube (Eppendorf) and a 0.2-ml PCR tube.

Step 2 is a process of transporting a reaction container between two or more incubators to rapidly change the temperature of the reaction solution in accordance with the temperature conditions required for the analysis method. When the temperature conditions are 37° C. for 15 minutes, 95° C. for 5 minutes, and 41° C. for 2 minutes, more specifically, three types of incubators at 37° C., 95° C., and 41° C. are prepared. At the outset, the reaction container is introduced into an incubator at 37° C. and retained therein for 15 minutes. Subsequently, the reaction container is transferred to an incubator at 95° C. and retained therein for 5 minutes. Finally, the reaction container is transferred to an incubator at 41° C. and retained therein for 2 minutes. The retention time is preferably prolonged by taking the time required for the temperature of the solution to reach the target level after transportation into consideration. Such time varies depending on differences in temperature changes, and the time required to reach the target temperature is as shown in Table 1 according to the results of the experiment conducted by the present inventors. Also, such temperature changes may occasionally cause the reaction solution to evaporate. The reaction solution can be prevented from evaporating by a method involving the addition of oil or a conventional method involving covering the reaction container and heating the cover.

TABLE 1

| Time required to reach target temperature | | |
| --- | --- | --- |
| Temperature before transportation | Target temperature | Time (sec.) |
| 28° C. | 65° C. | 42 |
| 28° C. | 37° C. | 44 |
| 37° C. | 95° C. | 116 |
| 65° C. | 41° C. | 44 |
| 95° C. | 41° C. | 100 |

Step 3 involves detection of the reaction with a detector. Any method may be employed in this step, provided that it allows a target substance to be detected in accordance with an analysis method. Preferably, the reaction containers are rotated with the use of a rotary disc to continuously analyze a plurality of reaction containers, and detection is carried out with the use of a detector in accordance with the rotation cycle. More preferably, the reaction is detected with the elapse of time.

According to this example, reaction containers can be subjected to continuous analysis even when assays involving different temperature changes during the process of preparation of sample solutions or assays involving different reaction or detection time or detection intervals are performed. Also, the processes for preparing samples can be completely synchronized. Further, temperature can be changed more rapidly than is possible with a conventional technique.

Example 2

In this example, an automatic analyzer that automatically performs the analysis described in Example 1 is described.

Figure 2:
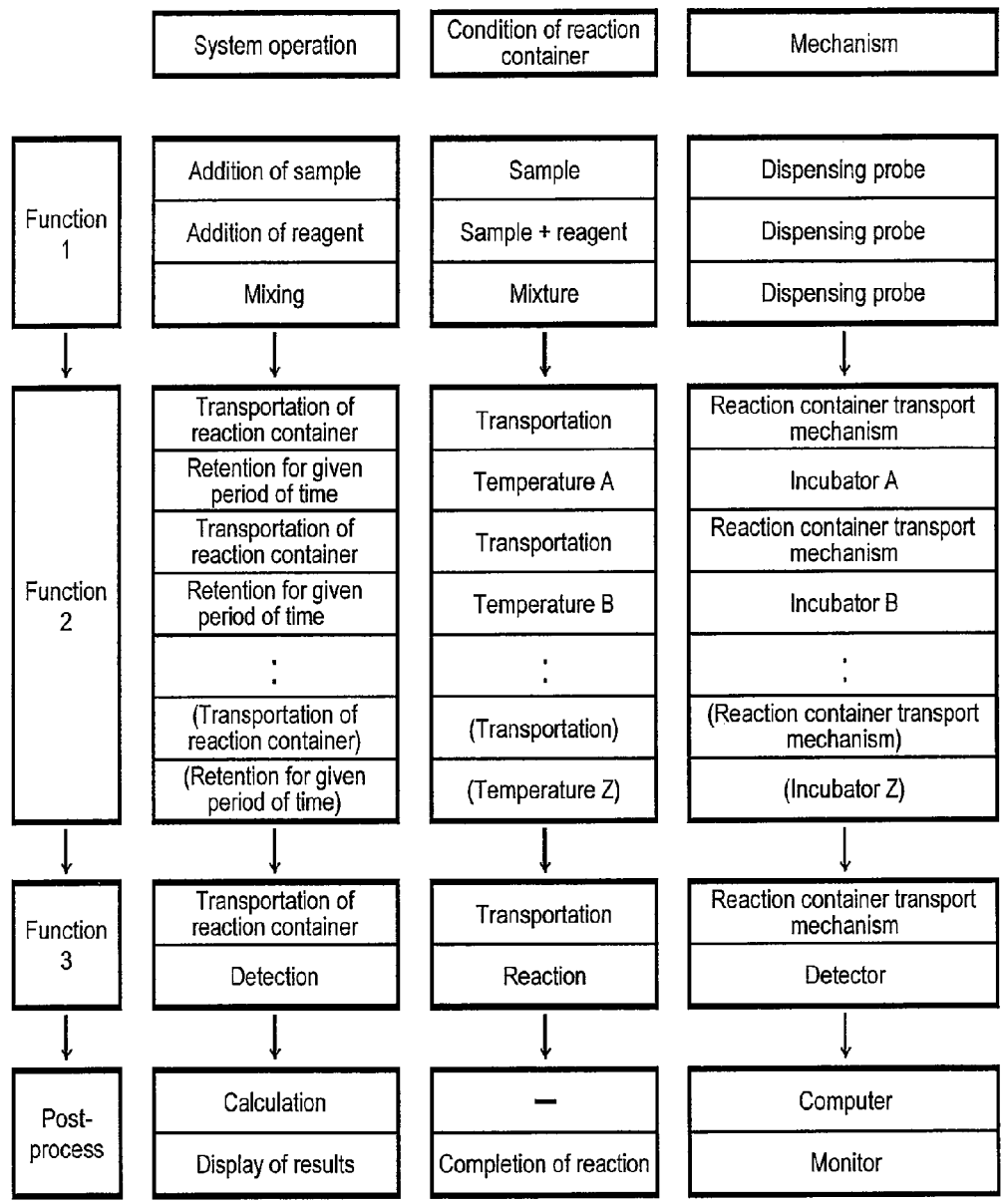
FIG. 2 is a schematic flow diagram illustrating operations of an automatic analyzer in the examples.
Figure 3:
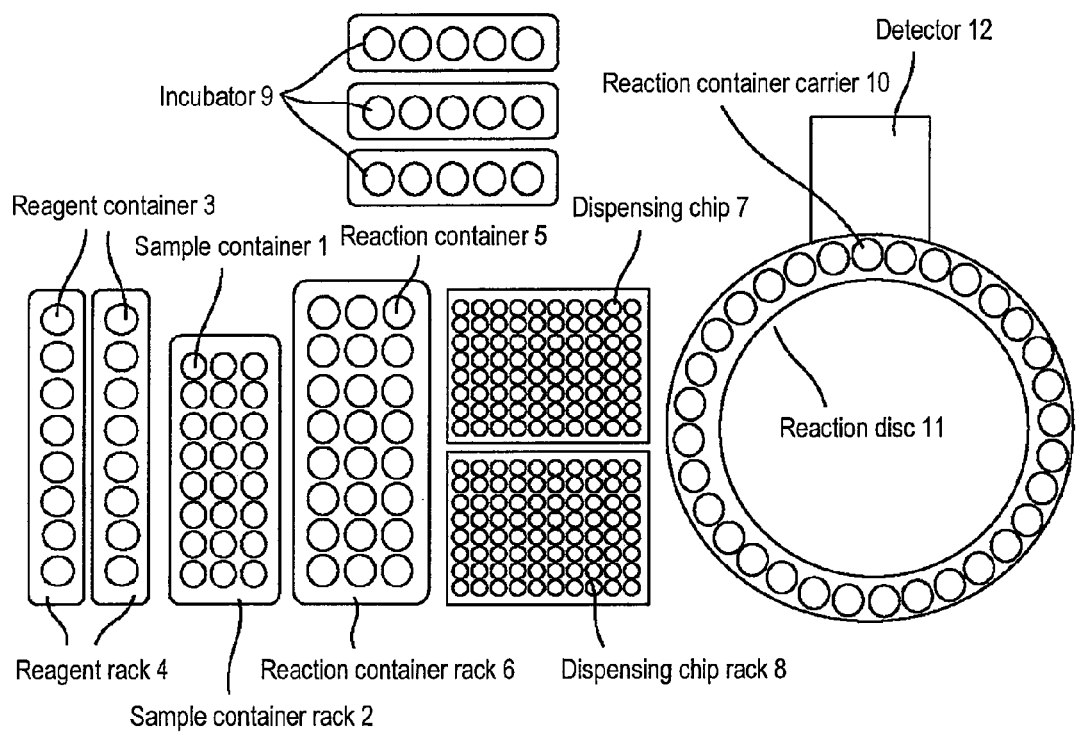
FIG. 3 schematically illustrates the basic construction of an automatic analyzer in the examples.
Figure 4:
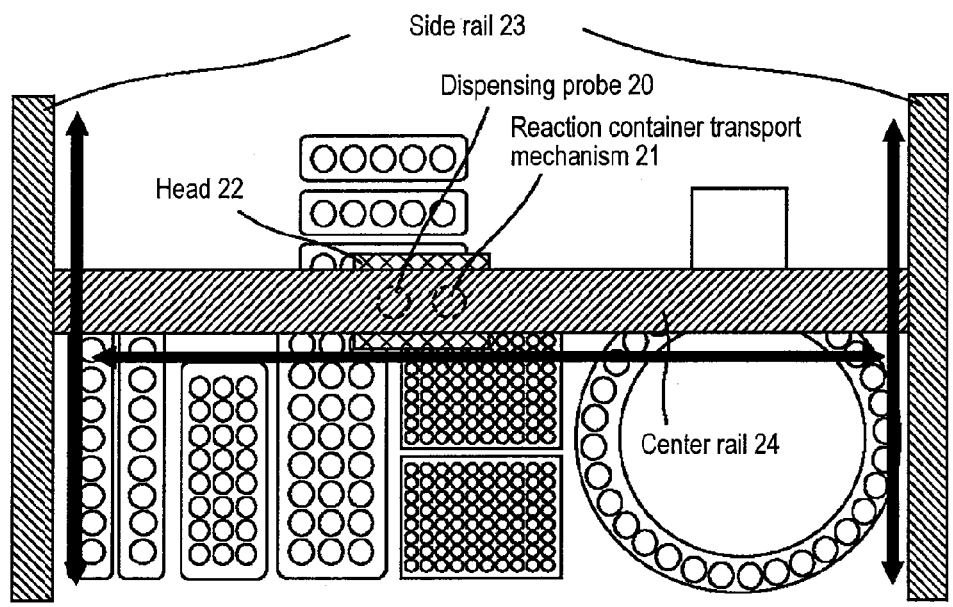
FIGS. 4(a) and 4(b) schematically illustrate a reaction container transport mechanism or the like in the examples.
Figure 4:
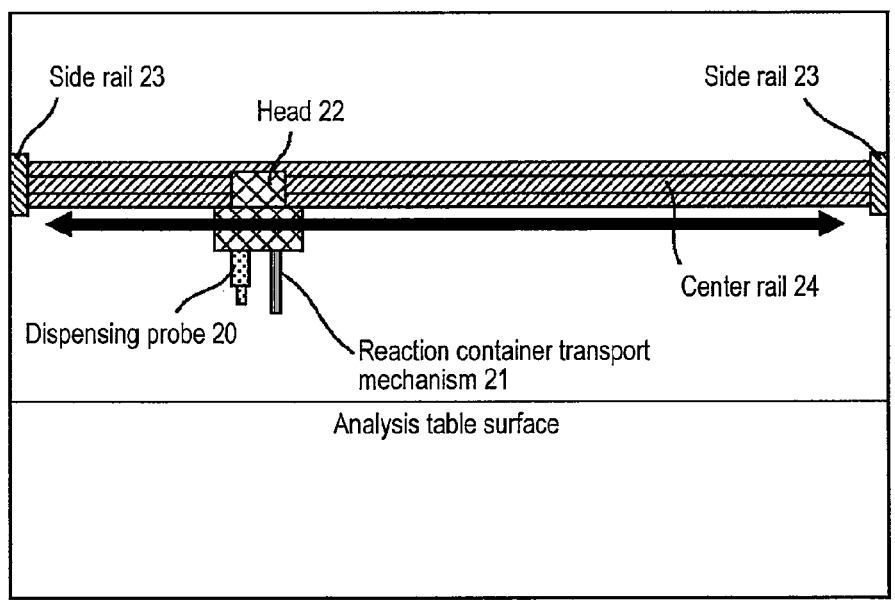

The automatic analyzer of this example is an apparatus that automatically implements an analysis method requiring two or more temperature changes in the process of reaction solution preparation, which is realized by the operations of the apparatus shown in FIG. 2 and the constitution of the apparatus shown in FIGS. 3 and 4. Hereafter, the automatic analyzer is described in detail with reference to FIGS. 2 to 5 mainly in comparison with Example 1.

FIG. 3 shows the basic construction of the automatic analyzer used herein, except for the dispensing probe and the reaction container transport mechanism. This apparatus comprises: a sample container rack 2 that can comprise a sample container 1 accommodating the test sample mounted thereon; a reagent rack 4 that accommodates a plurality of reagent containers 3 comprising a reagent reacting with various component of the sample; a reaction container rack 6 that accommodates a reaction container 5 used for mixing the sample with the reagent; a dispensing chip rack 8 that accommodates a dispensing chip 7; a plurality of incubators 9 set at two or more different temperatures; a reaction disc 11 that comprises a plurality of reaction container carriers 10 positioned around the circumference thereof; and a detector 12 that detects the reaction.

FIG. 4(a) and FIG. 4(b) are schematic diagrams illustrating a dispensing probe 20 for dispensing a sample or reagent between racks, a reaction container transport mechanism 21 for transporting a reaction container, a head 22 for connecting the same, and a side rail 23 and a center rail 24 for moving the head toward the X axis and the Y axis.

The automatic analyzer according to this example automatically analyzes a sample by the operations shown in FIG. 2. Specifically, the dispensing probe 20 moves to the position of the dispensing chip rack 8 via the motion of the side rail 23 and the center rail 24 and mounts the dispensing chip 7. The dispensing probe 20 on which the dispensing chip 7 had been mounted removes a sample from the sample container 1 and discharges the sample into the reaction container 5. Subsequently, the dispensing chip 7 is exchanged with a fresh chip, the reagent is removed from the reagent container 3 and discharged into the reaction container 5, and the dispensing probe 20 mixes the reaction solution via repetition of suction and ejection. The reaction container 5 containing the reaction solution is transferred to one of the incubators 9 by the reaction container transport mechanism 21, and the temperature of the reaction solution is changed. After the reaction container has been retained in an incubator for a given period of time, it is transferred to another incubator 9 by the reaction container transport mechanism, the temperature of the reaction solution is changed, and the resultant is also retained in an incubator for a given period of time. Transportation between incubators is carried out under conditions designated for the relevant analysis method. In accordance with the designated analysis method, the dispensing probe 20 with the dispensing chip 7 mounted thereon may remove a reagent from the reagent container 3 and discharge the reagent into the reaction container 5 after or during the process of temperature changes between the incubators. After temperature has been changed, the reaction container transport mechanism 21 introduces the reaction container 5 into the reaction container carrier 10 positioned within the reaction disc 11. The temperature of the reaction container carrier 10 is maintained at a level at which the reaction proceeds in the most effective manner. Such reaction is detected by the detector 12. More preferably, the detector 12 detects the reaction with the elapse of time in accordance with the cell cycle of the reaction disc 11.

Figure 5:
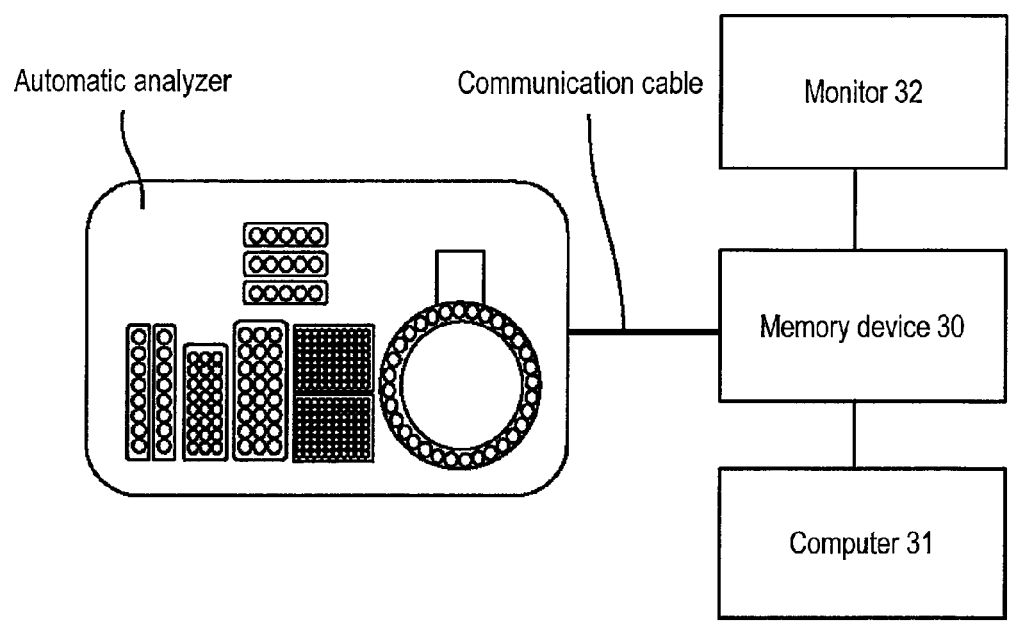
FIG. 5 schematically shows the correlation between an automatic analyzer and peripheral devices in the examples.

FIG. 5 shows the correlation between the automatic analyzer and peripheral devices. This automatic analyzer comprises a memory device 30 that stores the detection data, a computer 31 that computes the stored detection data, and a monitor 32 that displays the results of computation connected thereto. Such peripheral devices may be connected to the automatic analyzer via a connecting cable 33 and they may function independently. Alternatively, such peripheral devices may be built into the automatic analyzer.

As operations of the apparatus, including the post-treatment, the detection data detected by the detector 12 are transferred to the memory device 30, the data are computed by the computer 31, and the results of detection are displayed on the monitor 32.

The above examples disclose a transport mechanism that transports both the dispensing probe and the reaction container. The dispensing probe and the reaction container may be handled by different transport mechanisms. While the above examples involve the use of a single transport mechanism, a plurality of transport mechanisms may be provided, so as to cope with the use of a plurality of incubation mechanisms or analysis mechanisms, according to need.

DESCRIPTION OF NUMERICAL REFERENCES

1: Sample container
2: Sample container rack
3: Reagent container
4: Reagent rack
5: Reaction container
6: Reaction container rack
7: Dispensing chip
8: Dispensing chip rack
9: Incubator
10: Reaction container carrier
11: Reaction disc
12: Detector
20: Dispensing probe
21: Reaction container transport mechanism
22: Head
23: Side rail
24: Center rail
30: Memory device
31: Computer
32: Monitor
33: Connecting cable

The invention claimed is:

1. An automatic analyzer configured to execute an analytical reaction requiring two or more temperature changes in the process of preparing reaction samples, said analyzer comprising:

a plurality of reaction containers, each of the plurality of reaction containers containing one of the reaction samples;

a plurality of incubation mechanisms, each of the plurality of incubation mechanisms configured to control the temperatures of the plurality of reaction containers;

a transport mechanism configured to transport each of the plurality of reaction containers;

a control mechanism configured to control the transport mechanism;

a rotary disc configured to rotate the plurality of the reaction containers;

a detector disposed around a circumference of the rotary disc and configured to detect fluorescence emitted from each of the plurality of reaction containers rotating by the rotary disc; and an analytical mechanism configured to perform an analysis of each of the reaction samples based on the emission of the fluorescence, wherein:

the control mechanism is configured to control the transport mechanism to continuously transport each of the plurality of reaction containers within a given period of time and in a given order from one of the plurality of incubation mechanisms to another one of the plurality of incubation mechanisms in which two or more different temperature levels are set, and the transport mechanism is configured to transport each one of the plurality of reaction containers to the rotary disc continuously, after the given period of time.

2. The automatic analyzer according to claim 1, wherein the given period of time and the given order of each of the plurality of reaction containers are different based on the contents in said each of the plurality of reaction containers.

3. The automatic analyzer according to claim 2, wherein the analytical mechanism is further configured to continuously assay the emission of the fluorescence emitted from each of the plurality of reaction containers rotating by the rotary disc.

4. The automatic analyzer according to claim 1, wherein the reaction samples comprise nucleic acids and the analytical mechanism is configured to assay an increase in the amount of the nucleic acids in real-time.

5. The automatic analyzer according to claim 1, further comprising a dispensing mechanism configured to add a reagent to the plurality of the reaction containers.

6. The automatic analyzer according to claim 5 is configured to agitate the plurality of reaction containers when the reagent is added.

7. The automatic analyzer according to claim 1, wherein each of the plurality of the incubation mechanisms has an incubation time, and the incubation time in each of the plurality of the incubation mechanisms is altered depending on the temperature of said each of the plurality of the incubation mechanisms.

* * * * *